(12) United States Patent
Legrand et al.

(10) Patent No.: US 7,022,144 B2
(45) Date of Patent: Apr. 4, 2006

(54) OXIDIZING COMPOSITIONS CONTAINING A MIXTURE OF POLYMERS INCLUDING AT LEAST ONE COPOLYMER BASED ON ACRYLAMIDE AND 2-ACRYLAMIDO-2-METHYLPROPANESULPHONIC ACID

(75) Inventors: Frederic Legrand, Courbevoie (FR); Sylvain Kravtchenko, Asnieres (FR)

(73) Assignee: L'OREAL, (FR)

( * ) Notice: Subject to any disclaimer, the term of this patent is extended or adjusted under 35 U.S.C. 154(b) by 251 days.

(21) Appl. No.: 10/729,851

(22) Filed: Dec. 8, 2003

(65) Prior Publication Data

US 2004/0143912 A1 Jul. 29, 2004

Related U.S. Application Data

(60) Provisional application No. 60/444,638, filed on Feb. 4, 2003.

(30) Foreign Application Priority Data

Dec. 9, 2002 (FR) .................................. 02 15546

(51) Int. Cl.
*A61K 7/13* (2006.01)

(52) U.S. Cl. ........................ 8/405; 8/406; 8/552; 8/557; 8/587; 8/588; 8/111; 132/202; 132/208; 424/401; 424/70.17

(58) Field of Classification Search ..................... 8/405, 8/406, 552, 557, 587, 588, 111; 424/401, 424/70.17; 132/202, 208
See application file for complete search history.

(56) References Cited

U.S. PATENT DOCUMENTS

| | | | |
|---|---|---|---|
| 6,180,118 B1 * | 1/2001 | Maubru | 424/401 |
| 6,187,302 B1 | 2/2001 | Nguyen et al. | 424/70.1 |
| 6,238,658 B1 | 5/2001 | Nguyen et al. | 424/70.2 |
| 2002/0157193 A1 | 10/2002 | Legrand et al. | 8/405 |

FOREIGN PATENT DOCUMENTS

| | | |
|---|---|---|
| DE | 202 07 896 | 9/2002 |
| FR | 2816316 | 5/2002 |
| FR | 2818537 | 6/2002 |
| FR | 2818540 | 6/2002 |

* cited by examiner

*Primary Examiner*—Eisa Elhilo
(74) *Attorney, Agent, or Firm*—Steptoe & Johnson LLP

(57) ABSTRACT

The invention relates to an oxidizing composition for keratin fibers, in particular for human keratin fibers and more particularly the hair, comprising, in a cosmetically acceptable medium:
  at least one oxidizing agent chosen from the group formed by hydrogen peroxide and compounds capable of producing hydrogen peroxide by hydrolysis, or mixtures thereof,
  at least one copolymer (b) based on 2-acrylamido-2-methylpropanesulphonic acid and acrylamide, and
  at least one polymer (c) chosen from crosslinked 2-acrylamido-2-methylpropanesulphonic acid homopolymers or amphiphilic copolymers consisting of at least one sequence of 2-acrylamido-2-methylpropanesulphonic acid units and at least one unit comprising a hydrophobic portion.

The invention also relates to the dyeing, permanent-waving, bleaching and stripping processes and devices using the said composition.

37 Claims, No Drawings

OXIDIZING COMPOSITIONS CONTAINING A MIXTURE OF POLYMERS INCLUDING AT LEAST ONE COPOLYMER BASED ON ACRYLAMIDE AND 2-ACRYLAMIDO-2-METHYLPROPANESULPHONIC ACID

The present application claims the benefit of U.S. Provisional Application Ser. No. 60/444,638, filed Feb. 4, 2003.

The present invention relates to oxidizing compositions for treating keratin materials, comprising a mixture of polymers including at least one copolymer based on 2-acrylamido-2-methylpropanesulphonic acid and acrylamide, and to their uses for dyeing, for permanently reshaping or for bleaching or stripping human keratin fibres and in particular the hair.

It is known practice to bleach keratin fibres and in particular human hair with bleaching compositions containing one or more oxidizing agents. Among the oxidizing agents conventionally used, mention may be made of hydrogen peroxide or compounds capable of producing hydrogen peroxide by hydrolysis, such as urea peroxide or persalts, for instance perborates, percarbonates and persulphates, hydrogen peroxide being particularly preferred.

These bleaching compositions are generally in the form of anhydrous products (powders or creams) containing alkali compounds (amines and alkali silicates) and a peroxygenated reagent such as an ammonium or alkali metal persulphate, perborate or percarbonate, which is diluted at the time of use with an aqueous hydrogen peroxide composition.

Bleaching compositions may also result from the mixing, at the time of use, of the anhydrous peroxygenated reactive powder with an aqueous composition containing the alkali compounds and another aqueous composition containing the hydrogen peroxide.

It is moreover known practice to dye keratin fibres and in particular human hair with dye compositions containing oxidation dye precursors, in particular ortho- or para-phenylenediamines, ortho- or para-aminophenols, and heterocyclic compounds, generally known as oxidation bases. Oxidation dye precursors, or oxidation bases, are colourless or weakly coloured compounds which, when combined with oxidizing products, may give rise to coloured compounds or dyes via a process of oxidative condensation. It is also known that the shades obtained with these oxidation bases may be varied by combining them with couplers or coloration modifiers, the latter being chosen especially from aromatic meta-diamines, meta-aminophenols, meta-diphenols and certain heterocyclic compounds such as indole compounds.

To localize the bleaching or dyeing product on the hair so that it does not run onto the face or beyond the areas that it is proposed to bleach, use has been made hitherto of conventional thickeners such as crosslinked polyacrylic acid, hydroxyethylcelluloses, certain polyurethanes, waxes, and also, in the case of aqueous bleaching compositions, mixtures of ionic surfactants with HLB (hydrophilic lipophilic balance) values which, when suitably selected, give rise to the gelling effect when they are diluted using water and/or surfactants.

More recently, the use of amphiphilic polymers comprising at least one ethylenically unsaturated monomer containing a sulphonic group and more particularly acrylamido-2-methylpropanesulphonic acid polymers or copolymers, which form the subject of the patent application FR 2 818 537, to obtain hydrogen peroxide solutions that are thickened or in gel form and stable on storage, has been discovered.

However, the formulations thus thickened, or gelled, cause a problem of use during the mixing of the oxidizing agent with a dye support. Indeed, very substantial fluidizing of the two formulations takes place as soon as the mixing is begun. Even though this fluidizing phase is only transient, the use of these oxidizing formulations is problematic, most particularly for professionals.

The inventors have discovered, surprisingly, that it is possible to very greatly reduce this fluidizing observed during mixing, by combining at least one copolymer based on acrylamide and 2-acrylamido-2-methylpropanesulphonic acid with oxidizing formulations containing at least one polymer having at least one particular sequence of 2-acrylamido-2-methylpropanesulphonic acid units. The inventors have thus obtained thickened oxidizing compositions, which are stable on storage, irrespective of the source of aqueous hydrogen peroxide solution used, eliminating the problems of fluidizing, in particular in the case of mixing.

The invention also relates to processes for the oxidation dyeing of keratin fibres, to processes for treating the fibres, and in particular permanent-waving processes, to bleaching or stripping processes, and also to multi-compartment-dyeing devices or "kits".

Other characteristics, aspects, subjects and advantages of the invention featured in the description below will allow the invention to be defined more clearly.

For the purposes of the present invention, the term "stripping" means the total or partial destruction of the pigments or synthetic dyes present on or in keratin fibres resulting from a direct dyeing or oxidation dyeing process.

For the purposes of the present invention, the term "bleaching" means the total or partial destruction of the natural pigments present in keratin fibres (in particular eumelanins and phaeomelanins).

One subject of the present invention is thus an oxidizing composition for keratin fibres, in particular for human keratin fibres and more particularly the hair, comprising, in a cosmetically acceptable medium:

(a) at least one oxidizing agent chosen from the group formed by hydrogen peroxide and compounds capable of producing hydrogen peroxide by hydrolysis, or mixtures thereof, (b) at least one copolymer based on 2-acrylamido-2-methylpropanesulphonic acid and acrylamide, and (c) at least one polymer chosen from crosslinked 2-acrylamido-2-methylpropanesulphonic acid homopolymers or amphiphilic copolymers consisting of at least one sequence of 2-acrylamido-2-methylpropanesulphonic acid units and at least one unit comprising a hydrophobic portion.

For the purposes of the present invention, the term "hydrophobic portion" means a branched or non-branched, saturated or unsaturated hydrocarbon-based fatty chain containing from 6 to 50 carbon atoms.

The polymers contained in the composition in accordance with the invention are in free form or are partially or totally neutralized with a mineral base (sodium hydroxyl, potassium hydroxyl or aqueous ammonia) or an organic base such as monoethanolamine, diethanolamine or triethanolamine, an aminomethylpropanediol, N-methylglucamine, basic amino acids, such as arginine and lysine, and mixtures of these compounds.

The copolymer (b) is formed from 2-acrylamido-2-methylpropanesulphonic acid and acrylamide. Commercial products that may be mentioned include the products sold in the form of an inverse emulsion under the references Sepigel 30 J or Simulgel 600 by SEPPIC.

The polymers (c) contain at least one sequence of 2-acrylamido-2-methylpropanesulphonic acid units. Thus, when these polymers do not consist only of this sequence, they are poly(2-acrylamido-2-methylpropanesulphonic acid)homopolymers. The passage in patent FR 2 753 372 devoted to the description of these homopolymers is incorporated into the present patent application.

According to the invention, the poly(2-acrylamido-2-methylpropanesulphonic acid) polymers are crosslinked, preferably with trimethylolpropane triacrylate and comprise, randomly distributed:

from 90% to 99.9% by weight of units of general formula (1) below:

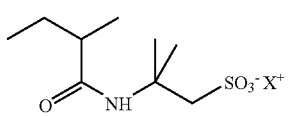

in which $X^+$ denotes a cation, preferably the ammonium ion, or a mixture of cations, not more than 10 mol % of the cations possibly being protons $H^+$;

from 0.01% to 10% by weight of crosslinking units derived from at least one monomer containing at least two olefinic double bonds; the weight proportions being defined relative to the total weight of the polymer.

The crosslinked poly(2-acrylamido-2-methylpropanesulphonic acid)homopolymer preferably comprises a number of units of formula (1) that is large enough to obtain polymer particles whose hydrodynamic volume in a water solution has a ratio ranging from 10 to 500 nm and whose distribution is uniform and unimodal.

The crosslinked poly(2-acrylamido-2-methylpropanesulphonic acid) polymers are present in the cosmetic compositions of the invention in concentrations ranging from 0.01% to 10% and more particularly from 0.05% to 5% by weight relative to the total weight of the composition.

When the polymers (c) contain more than one sequence of 2-acrylamido-2-methylpropanesulphonic acid units, the copolymer is chosen from amphiphilic copolymers consisting of at least one sequence of 2-acrylamido-2-methylpropanesulphonic acid units, and of at least one unit comprising a hydrophobic portion. These amphiphilic polymers are described in patent application FR 2 818 540. The passage of this patent application devoted to the description of these amphiphilic polymers is incorporated into the present patent application.

The amphiphilic copolymers have a weight-average molecular weight ranging from 20 000 to 10 000 000, preferably from 50 000 to 8 000 000 and more particularly from 100 000 to 7 000 000.

These copolymers may be crosslinked. When they are, the crosslinking agents may be chosen from the polyolefinically unsaturated compounds commonly used for crosslinking polymers obtained by free-radical polymerization. These agents are preferably chosen from methylenebisacrylamide, allyl methacrylate and trimethylolpropane triacrylate (TMPTA). The degree of crosslinking preferably ranges from 0.01 to 10 mol % and more particularly from 0.2 to 2 mol % relative to the polymer.

The amphiphilic copolymers comprise at least one sequence of an ethylenically unsaturated hydrophobic monomer comprising at least one hydrophobic portion ranging from 6 to 50 carbon atoms, preferably from 6 to 22 and more particularly from 12 to 18 carbon atoms.

This ethylenically unsaturated hydrophobic monomer is chosen from the acrylates or acrylamides of formula (2) below:

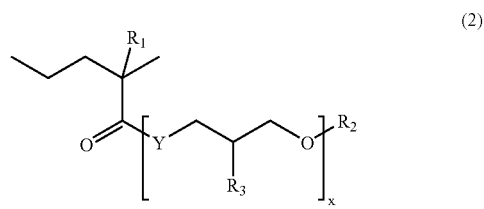

in which $R_1$ and $R_3$, which may be identical or different, denote a hydrogen atom or a linear or branched $C_1$–$C_6$ alkyl radical, preferably methyl; Y denotes O or NH ; $R_2$ denotes a hydrophobic hydrocarbon-based radical containing from 6 to 50 carbon atoms, more preferably from 6 to 22 carbon atoms and even more preferably from 6 to 18 carbon atoms; x denotes a number of moles of alkylene and ranges from 0 to 100.

The amphiphilic polymers described above are present in concentrations ranging from 0.01% to 30% by weight, more preferably from 0.1% to 10% by weight and even more preferably from 0.5% to 2% by weight relative to the total weight of the composition.

Another subject of the invention is a process for the oxidation dyeing of human keratin fibres and in particular the hair using a dye composition comprising, in a support that is suitable for dyeing keratin fibres, at least one oxidation dye precursor and an oxidizing composition as defined above. At the time of use, the dye composition is mixed with the oxidizing composition described; the mixture obtained is then applied to the keratin fibres and left to act for 3 to 50 minutes approximately and preferably 5 to 30 minutes approximately, followed by a step of rinsing, washing with shampoo, rinsing again and finally drying. The dye composition and the oxidizing composition described may be applied sequentially, and in any order, with or without intermediate rinsing.

Another subject of the present invention is a process for treating human keratin fibres and in particular the hair, in order to permanently reshape these fibres, in particular in the form of permanent-waved hair, this process comprising the following steps.

A reducing composition is applied to the keratin material to be treated, the keratin fibre being placed under mechanical tension before, during or after the said application. This is performed lock by lock or to all the keratin fibres.

The head of hair onto which the reducing composition has been applied should conventionally be left at rest for a few minutes, generally 5 minutes to one hour. The reducing agent thus has time to act on the hair. This waiting phase preferably takes place at a temperature ranging from 35° C. to 45° C., preferably also while protecting the hair with a hood.

The keratin fibre impregnated with the reducing composition is optionally rinsed with an aqueous composition.

The oxidizing composition of the invention is applied to the optionally rinsed keratin fibre, in order to fix the new shape given to the hair. Again, the treated head of hair is left at rest for 3 to 30 minutes and preferably between 5 and 15 minutes.

The keratin fibre again undergoes a rinsing operation, generally with water.

The oxidizing composition according to the invention may also be used in a process for bleaching or stripping human keratin fibres and in particular the hair, comprising the following steps: application of the oxidizing composition according to the invention to the keratin fibre, followed by a step of rinsing the keratin fibre thus treated.

Another subject of the invention is a 2-compartment device for dyeing or permanently reshaping or bleaching keratin fibres, in particular human keratin fibres. A first compartment contains either a dye composition or a reducing composition or a first oxidizing composition, and a second compartment contains the oxidizing composition defined above.

In the context of bleaching, the first composition is preferably an anhydrous powder or paste containing at least one persalt.

The examples that follow illustrate the invention without being limiting in nature.

EXAMPLE 1

The Applicant performed a comparative test in order to demonstrate the improvement provided in terms of fluidizing during the mixing of the oxidizing composition and the dye composition.

The Applicant prepared 3 compositions, 2 in accordance with the prior art and 1 in accordance with the invention (table below).

|  | Formula A in accordance with the prior art | Formula B in accordance with the prior art | Formula C in accordance with the invention |
|---|---|---|---|
| Aqueous hydrogen peroxide solution | 6% | 6% | 6% |
| Crosslinked polyacrylamidomethylpropanesulphonic acid partially neutralized to 50% with aqueous ammonium, sold by Clariant under the name Hostacerin AMPS | 1.5% | / | 1.5% |
| Acrylamide/acrylamidomethylpropanesulphonic copolymer, sodium salt, as an inverse emulsion in isohexadecane/water, sold by SEPPIC under the name Simulgel 600 | / | 1% | 1% |
| pH agent | qs pH = 3.6 | qs pH = 3.6 | qs pH = 3.6 |
| Water | qs 100 g | qs 100 g | qs 100 g |

The stability of these oxidizing gels was studied over time. This assessment was performed by a panel of 5 experts.

The composition of formula B is unstable. Indeed, it shows a drop in viscosity after 2 months at 45° C. On the other hand, the compositions of formulae A and C remain stable.

The dye support used to prepare the mixtures is the commercial support Excellence shade 5 from the company L'Oréal. The fluidizing was evaluated by a panel of 5 experts.

The compositions of formulae A and B show substantial fluidizing as soon as the mixing is begun.

The composition of formula C has no significant observed fluidizing.

These comparative tests clearly show the superior effect of the combination of the two polymers, compared with the compositions comprising only one polymer.

EXAMPLE 2

Similarly, when an amphiphilic copolymer according to the invention is combined with the 2-acrylamido-2-methylpropanesulphonic acid polymer according to formula D, no fluidizing is observed during the mixing with the commercial dye support Excellence shade 5 sold by the company L'Oréal. This study was evaluated by a panel of 5 experts.

|  | Formula D in accordance with the invention |
|---|---|
| Aqueous hydrogen peroxide solution | 6% |
| Sodium stannate | 0.04% |
| Sodium pyrophosphate | 0.03% |
| Isostearyl alcohol | 2% |
| 80/20 AMPS/ethoxylated(25 EO)cetearyl copolymer, crosslinked with trimethylolpropane triacrylate (TMPTA) sold by Clariant under the name Aristoflex HMS | 1% |
| Acrylamide/acrylamidomethylpropanesulphonic copolymer, sodium salt, as an inverse emulsion in isohexadecane/water, sold by SEPPIC under the name Simulgel 600 | 1% |
| pH agent | qs pH = 3.5 |
| Water | qs 100 g |

The invention claimed is:

1. An oxidizing composition for keratin fibres, comprising, in a cosmetically acceptable medium:
   (a) at least one oxidizing agent which is hydrogen peroxide or a compound capable of producing hydrogen peroxide by hydrolysis, or a mixture thereof,
   (b) at least one copolymer based on acrylamido-2-methylpropanesulphonic acid and acrylamide, and
   (c) at least one polymer which is a crosslinked 2-acrylamido-2-methylpropanesulphonic acid homopolymer or amphiphilic copolymer comprising at least one sequence of 2-acrylamido-2-methylpropanesulphonic acid units and at least one unit comprising a hydrophobic portion.

2. The composition according to claim 2, wherein the keratin fibres are human keratin fibre.

3. The composition according to claim 2, wherein the keratin fibres are hair.

4. The composition according to claim 1, wherein the composition comprises:
   (a) hydrogen peroxide,
   (b) at least one copolymer based on acrylamido-2-methylpropanesulphonic acid and acrylamide, and
   (c) at least one crosslinked 2-acrylamido-2-methylpropanesulphonic acid homopolymer.

5. The composition according to claim 1, wherein the composition comprises:
   (a) hydrogen peroxide,
   (b) at least one copolymer based on acrylamido-2-methylpropanesulphonic acid and acrylamide, and
   (c) at least one amphiphilic copolymer comprising at least one sequence of 2-acrylamido-2-methylpropanesulphonic acid units and at least one unit comprising a hydrophobic portion.

6. The composition according to claim 5, wherein the composition comprises, as the amphiphilic copolymer (c), a 2-acrylamido-2-methylpropanesulphonic acid/ethoxylated cetearyl methacrylate copolymer crosslinked with trimethyloipropane triacrylate.

7. The composition according to claim 4, wherein the crosslinked poly(2-acrylamido-2-methylpropanesulphonic acid) homopolymer (c) comprises, randomly distributed: from 90% to 99.9% by weight of units of formula (1) below:

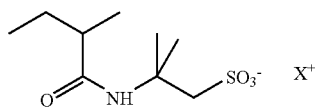

(1)

in which $X^+$ denotes a cation or a mixture of cations, not more than 10 mol % of the cations optionally being protons $H^+$; and from 0.01% to 10% by weight of crosslinking units derived from at least one monomer containing at least two olefinic double bonds; the weight proportions being defined relative to the total weight of the polymer.

8. The composition of claim 7, wherein the cation is an ammonium ion.

9. The composition according to claim 5, wherein the amphiphilic copolymer has a weight-average molecular weight ranging from 20,000 to 10,000,000.

10. The composition of claim 9, wherein the amphiphilic copolymer has a weight-average molecular weight ranging from 50,000 to 8,000,000.

11. The composition of claim 9, wherein the amphiphilic copolymer has a weight-average molecular weight ranging from 100,000 to 7,000,000.

12. The composition according to claim 5, wherein the amphiphilic copolymer comprises at least one sequence of a monomer which is an ethylenically unsaturated hydrophobic monomer comprising at least one hydrophobic portion containing from 6 to 50 carbon atoms.

13. The composition according to claim 12, wherein the hydrophobic portion contains 6 to 22 carbon atoms.

14. The composition according to claim 12, wherein the hydrophobic portion contains 12 to 18 carbon atoms.

15. The composition according to claim 12, wherein the ethylenically unsaturated hydrophobic monomer is an acrylate or acrylamide of formula (2) below:

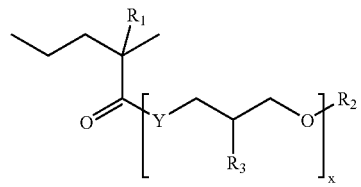

(2)

in which $R_1$ and $R_3$, which may be identical or different, denote a hydrogen atom or a linear or branched $C_1$–$C_6$ alkyl radical; Y denotes O or NH ; $R_2$ denotes a hydrophobic hydrocarbon-based radical containing from 6 to 50 carbon atoms; x denotes a number of moles of alkylene and ranges from 0 to 100.

16. The composition according to claim 15, wherein the $C_1$–$C_6$ alkyl radical is methyl.

17. The composition according to claim 15, wherein the hydrophobic hydrocarbon-based radical contains from 6 to 22 carbon atoms.

18. The composition according to claim 15, wherein the hydrophobic hydrocarbon-based radical contains from 6 to 18 carbon atoms.

19. A process for the oxidation dyeing of keratin fibres, comprising applying to the keratin fibres:
   (i) a dye composition comprising, in a support that is suitable for dyeing keratin fibres, at least one oxidation dye precursor, and
   (ii) the oxidizing composition as defined in claim 1.

20. The dyeing process according to claim 19, wherein:
   (i) the dye composition is mixed, at the time of use, with the oxidizing composition,
   (ii) the mixture obtained is then applied to the keratin fibres,
   (iii) the mixture is left to act for approximately 3 to 50 minutes, and then
   (iv) the keratin fibres are rinsed, washed with shampoo, rinsed again and finally dried.

21. The process according to claim 20, wherein the mixture is left to act for approximately 5 to 30 minutes.

22. The process according to claim 20, wherein the dye composition and the oxidizing composition are sequentially applied to the keratin fibres, in any order, with or without intermediate rinsing.

23. A process for treating keratin fibres in order to permanently reshape the fibres, comprising the following steps:
   (i) applying a reducing composition to the keratin fibres, the keratin fibres being placed under mechanical tension before, during or after the application of the reducing composition,
   (ii) optionally rinsing the keratin fibres,
   (iii) applying the oxidizing composition of claims 17 to the optionally rinsed keratin fibres, and
   (iv) rinsing the fibres treated with the oxidizing composition.

24. The process of claim 23, wherein the fibres are human hair.

25. The process of claim 23, wherein the fibres are reshaped in the form of permanent-waved hair.

26. A process for bleaching or stripping keratin fibres, comprising the following steps: applying the oxidizing composition of claim 17 to the keratin fibres, and (ii) rinsing the fibres treated with the oxidizing composition.

27. The process according to claim 26, wherein the keratin fibres are human hair.

28. The process according to claim 26, wherein the keratin fibres are hair.

29. A two-compartment device for dyeing keratin fibres, comprising a first compartment containing a dye composition and a second compartment containing the oxidizing composition of claim 17.

30. The device according to claim 29, wherein the fibres are human keratin fibres.

31. The device according to claim 29, wherein the fibres are hair.

32. A two-compartment device for permanently reshaping keratin fibres, comprising a first compartment containing a composition comprising at least one reducing agent that is suitable for permanently reshaping keratin fibres and a second compartment containing the oxidizing composition of claim 17.

33. The device according to claim 32, wherein the keratin fibres are human keratin fibres.

34. The device according to claim 32, wherein the keratin fibres are hair.

35. A two-compartment device for bleaching keratin fibres, comprising a first compartment containing an anhydrous powder or paste containing at least one persalt, and a second compartment containing the oxidizing composition of claim 17.

36. The device according to claim 35, wherein the keratin fibres are human keratin fibres.

37. The device according to claim 35, wherein the keratin fibres are hair.

* * * * *